United States Patent [19]
Stracke et al.

[11] Patent Number: 5,449,753
[45] Date of Patent: Sep. 12, 1995

[54] AUTOTAXIN: MOTILITY STIMULATING PROTEIN USEFUL IN CANCER DIAGNOSIS

[75] Inventors: Mary Stracke, Silver Spring; Lance A. Liotta, Potomac; Elliott Schiffmann, Chevy Chase; Henry Krutzsch, Bethesda, all of Md.

[73] Assignee: The United States of America as represented by the Department of Health and Human Services, Washington, D.C.

[21] Appl. No.: 822,043

[22] Filed: Jan. 17, 1992

[51] Int. Cl.$^6$ .................. A61K 38/00; C07K 5/00; C07K 7/00; C07K 17/00
[52] U.S. Cl. .................. 530/326; 530/327; 530/328; 530/329; 530/330; 530/350
[58] Field of Search .................. 530/326, 327, 328, 329, 530/330, 350; 525/54.11

[56] References Cited

U.S. PATENT DOCUMENTS 5,003,047 3/1991 Yarmush et al. ............ 530/413

OTHER PUBLICATIONS

Merck Index 11th Ed, p. 1307.
Liotta et al. PNAS USA vol. 83, 3302–06 (May 1986).
M. Stracke, R. Guirguis, L. Liotta, E. Schiffmann, Pertussis Toxin Inhibits Stimulated Motility..., Biochemical & Biophysical Research Commun., vol. 146, No. 1, Jul. 15, 1987, pp. 339–345.
M. Stracke, E. Kohn, S. Aznavoorian, L. Wilson, D. Salomon, H. Krutzsch, L. Liotta, E. Schiffmann, Insulin–Like Growth Factors Stimulate..., Biochemical and Biophysical Res. ..., vol. 153, No. 53, Jun. 30, 1988, pp. 1076–1083.
M. Stracke, J. Engel, L. Wilson, M. Rechler, L. Liotta, E. Schiffmann, The Type I Insulin–Like Growth Factor Receptor is a..., The Journal of Biological Chemistry, vol. 264, No. 36, Dec. 25, 1989, pp. 21544–21549.
M. Stracke, H. Krutzsch, E. Schiffmann, L. Liotta, Signal Transduction for Chemotaxis and..., The Journal of Cell Biology, vol. 110, Apr. 1990, pp. 1427–1438.
M. Stracke, H. Krutzsch, E. Unsworth, A. Arestad, V. Cioce, E. Schiffmann, L. Liotta, Identification, Purification, and Partial Sequence ..., The Journal of Biological Chem., vol. 267, No. 4, Feb. 5, 1992, pp. 2524–2529.
L. Liotta, R. Mandler, G. Murano, D. Katz, R. Gordon, P. Chiang, E. Schiffmann, Tumor Cell Autocrine Motility Factor, Proc. Natl. Acad. Sci. USA, vol. 83, pp. 3302–3306, May 1986.
Ann. Rev. Cell Biol. 1986, 2:337–365, "The Directed Migration of Eukaryotic Cells", S. J. Singer and Abraham Kupfer.
Imperial Cancer Research Fund 1988, Cancer Surveys, vol. 7, No. 4, 1988, "Tumour Motility Factors", pp. 631–653.
Nature, vol. 227, Aug. 15, 1970, "Cleavage of Structural Proteins during the Assembly of the Head of Bacteriophage T4", U. K. Laemmli, pp. 680–685.
The Journal of Biological Chemistry, vol. 250, No. 10, Issue of May 25, pp. 4007–4021, 1975, "High Resolution Two–Dimensional Electrophoresis of Proteins", Patrick H. O'Farrell.
Cell, vol. 12, 1133–1142, Dec. 1977, copyright 1977 by MIT, "High Resolution Two–Dimensional Electrophoresis ... Proteins", P. Z. O'Farrell, et al.
Electrophoresis 1988, 9, 255–262, Improved protein staining with nanogram sensitivity.
A Practical Guide to Protein and Peptide Purification for Microsequencing, by Paul T. Matsudaira, copyright 1989, pp. 31–47, "2 Enzymatic ... of Proteins".
Proc. Natl. Acad. Sci. USA, vol. 85, pp. 2444–2448, Apr. 1988, Biochemistry, "Improved tools for biological sequence comparison", W. Pearson & D. Lipman.

(List continued on next page.)

Primary Examiner—Howard E. Schain
Assistant Examiner—Sheela J. Huff
Attorney, Agent, or Firm—Foley & Lardner

[57] ABSTRACT

The present invention relates, in general, to autotaxin. In particular, the present invention relates to a DNA segment encoding autotaxin; recombinant DNA molecules containing the DNA segment; cells containing the recombinant DNA molecule; a method of producing autotaxin; and antibodies to autotaxin.

3 Claims, 7 Drawing Sheets

Nature, vol. 256, Aug. 7, 1975, "Continuous cultures of fused cells secreting antibody of predefined specificity", pp. 495–497.

Proc. Natl. Acad. Sci. USA, vol. 77, No. 9, pp. 5258–5262, Sep. 1980, Cell Biology, "Transforming growth factors produced by certain human tumor cells: Polypeptides that interact with epidermal growth factor receptors", George J. Todaro, Charlotte Eryling, and Joseph E. DeLarco.

Biochemical and Biophysical Research Communications, vol. 146, No. 3, 1987, Aug. 14, 1987, "Chemotactic Response of Rat Mammary Adenocarcinoma Cell Clones to Tumor-derived Cytokines", pp. 996–1002, Atnip, et al.

Journal of Cell Science 90, 391–399 (1988), "Foetal and cancer patient fibroblasts produce an autocrine migration-stimulating . . . adult cells", Schor, et al.

Proc. Natl. Acad. Sci. USA, vol. 86, pp. 2438–2442, Apr. 1989, Medical Sciences, "Purification of the migration stimulating factor produced by fetal and breast cancer patient fibroblasts", Grey, et al.

J. Neurosurg, vol. 73, Dec. 1990, "Motility factor produced by malignant glioma cells: role in tumor invasion", pp. 881–888, T. Ohnishi, M. D., et al.

Cancer Reseach 51, 3507–3511, Jul. 1, 1991, "Purification of B16-F1 Melanoma Autocrine Motility Factor and Its Receptor[1]", Steve Silletti, et al.

The Journal of Biological Chemistry, vol. 266, No. 20, Issue of Jul. 15, pp. 13442–13448, 1991, "Purification of Human Tumor Cell Autocrine Motility Factor and Molecular Cloning of Its Receptor", Hideomi Watanabe, et al.

The Journal of Cell Biology, vol. 98, Apr. 1984, pp. 1474–1480, "Laminin and Fibronectin Promote the Haptotactic Migration of B16 Mouse Melanoma Cells in Vitro", James B. McCarthy and Leo T. Furcht.

The Journal of Cell Biology, vol. 105, Nov. 1987, pp. 2409–2415, "Thrombospondin-induced Tumor Cell Migration: Haptotaxis and Chemotaxis are Mediated by Different Molecular Domains", Giulia Taraboletti, et al.

Clinical Immunology and Immunopathology 37, 387–396 (1985), "Neuropeptides are Chemoattractants for Human Tumor Cells and Monocytes: A Possible Mechanism for Metastasis", Michael Ruff et al.

Cancer Research 47, pp. 6324–6328, Dec. 1, 1987, "Nerve Growth Factor Stimulation of Mouse Embryonal Carcinoma Cell Migration[1]", Kahan, et al.

J. Exp. Med. 170:1649–1669, "Interleukin 6 Decreases Cell–Cell Association and Increases Motility of Ductal Breast Carcinoma Cells", Tamm, et al.

Biochemical and Biophysical Research Communications, vol. 169, No. 1, 1990, May 31, 1990, pp. 165–170, "Induction of Haptotactic Migration of Melanoma Cells by Neutrophil Activating Protein/Interleukin-8", Wang et al.

Proc. Natl. Acad. Sci. USA, vol. 88, pp. 2893–2897, Apr. 1991, Cell Biology, "Secreted or nonsecreted forms of acidic fibroblast growth factor produced by transfected epithelial cells . . . invasive potential", Jouanneau, et al.

Nature, vol. 327, 21 May 1987, 327:239–242, "Scatter factor is a fibroblast-derived modulator of epithelial cell mobility", Stoker, et al.

In Vitro Cellular & Developmental Biology, vol. 25, No. 2, Feb. 1989, pp. 163–173, "Smooth Muscle Releases an Epithelial Cell Scatter Factor Which Binds to Heparin", Rosen et al.

Proc. Natl. Acad. Sci. USA, vol. 86, pp. 5844–5848, Aug. 1989, Cell Biology, "Purification of scatter factor, a fibroblast-derived basic . . . and movement", Gherardi, et al.

Proc. Soc. Exp. Bilol. Med., 195:34–43, 1990, "Purified Scatter Factor Stimulates Epithelial and Vascular Endothelial Cell Migration (43115)", Rosen, et al.

The Hournal of Cell Biology, vol. 111, Nov. 1990, pp. 2097–2108, "Scatter Factor: Molecular Characteristics and . . . Cells", Weidner, et al.

PNAS 57:1782–1789, "Subunit Structure of a High--Molecular-Weight Form of the Nerve Growth Factor from Mouse Submaxillary Gland", Varon, et al.

Science, 225:932–935, Aug. 31, 1984, "Heparin Binds Endothelial Cell Growth Factor, the Principal Endothelial Cell Mitogen in Bovine Brain", Thomas Maciag, et al.

Proc. Natl. Acad. Sci., vol. 81, pp. 6963–6967, Nov. 1984, Biochemistry, "Isolation of brain fibroblast growth factor by Heparin-Sepharose affinity chromatography: Identity with pituitary fibroblast growth factor", Gospodarowicz, et al.

Proc. Natl. Acad. Sci., vol. 84, pp. 9233–9237, Dec. 1987, Medical Sciences, "Purification of a human . . . defense cytokines", Yoshimura, et al.

Annu. Rev. Immunol. 1990, 8:253–278, "Interleukin-6: An Overview", Jacques Van Snick.

Biochemical and Biophysical Research Communications, vol. 127, No. 2, Mar. 15, 1985, pp. 450–457, "Potential role . . . Leukocytes", Verghese[1] et al.

Macmillan Journals, Ltd., Nature, vol. 329, No. 6136, pp. 261–263, Sep. 17, 1987, "Cytokine-indiced pseudopodial . . . Migration", Guirguis et al.

Journal of Cell Science 89, pp. 123–127 (1988), Commentary, "Inositol phosphates, G-proteins and ras genes . . . Dictyostelium", Newell, et al.

Int. J. Cancer: 46, pp. 287–292 (1990), "Heterogeneity of the Motility Responses in Malignant Tumor Cells: A Biological Basis for the Diversity and Homing of Metastatic Cells", Elise C. Kohn, et al.

Cancer Research 50, pp. 409–414, Jan. 15, 1990, "Identification of B16-F1 Melanoma Autocrine Motility-Like Factor Receptor", Ivan R. Nabi, et al.

Yoshida et al., "Studies on the Mechanics of Invasion in Cancer", *Int. J. Cancer*, 6:123–132 (1970).

Warn et al., "Motility Factors on the March", *Nature*, 340:186–187 (1989).

UPPER WELLS

|  | 0 | 0.01% | 0.1% |
|---|---|---|---|
| 0 | 4.8 ± 0.3 | 13.7 ± 0.8 | 33.8 ± 1.6 |
| LOWER WELLS 0.01% | 45.4 ± 4.0 | 39.3 ± 2.6 | 36.9 ± 1.4 |
| 0.1% | 75.6 ± 1.8 | 58.3 ± 3.1 | 41.0 ± 3.4 |

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
( A ) LENGTH: 6 amino acids (B) TYPE: amino acid
(D) TOPOLOGY: linear (xi) SEQUENCE DESCRIPTION: SEQ ID NO:1:

Trp His Val Ala Ala Asn
1               5

(2) INFORMATION FOR SEQ ID NO:2:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:2:

Pro Xaa Leu Asp Val Tyr Lys
1               5

(2) INFORMATION FOR SEQ ID NO:3:

(i) SEQUENCE CHARACTERISTICS:
(A) LENGTH: 5 amino acids
(B) TYPE: amino acid
(D) TOPOLOGY: linear (xi) SEQUENCE DESCRIPTION: SEQ ID NO:3:

Tyr Pro Ala Phe Lys
1               5

(2) INFORMATION FOR SEQ ID NO:4:

(i) SEQUENCE CHARACTERISTICS:
(A) LENGTH: 5 amino acids
(B) TYPE: amino acid
(D) TOPOLOGY: linear (xi) SEQUENCE DESCRIPTION: SEQ ID NO:4:

Gln Ala Glu Val Ser
1               5

(2) INFORMATION FOR SEQ ID NO:5:

(i) SEQUENCE CHARACTERISTICS:
(A) LENGTH: 10 amino acids
(B) TYPE: amino acid
(D) TOPOLOGY: linear (xi) SEQUENCE DESCRIPTION: SEQ ID NO:5:

Pro Glu Glu Val Thr Xaa Pro Asn Tyr Leu
1               5                   10

(2) INFORMATION FOR SEQ ID NO:6:

(i) SEQUENCE CHARACTERISTICS:
(A) LENGTH: 9 amino acids
(B) TYPE: amino acid
(D) TOPOLOGY: linear (xi) SEQUENCE DESCRIPTION: SEQ ID NO:6:

Tyr Asp Val Pro Trp Asn Glu Thr Ile
1               5

(2) INFORMATION FOR SEQ ID NO:7:

(i) SEQUENCE CHARACTERISTICS:
(A) LENGTH: 10 amino acids
(B) TYPE: amino acid
(D) TOPOLOGY: linear (xi) SEQUENCE DESCRIPTION: SEQ ID NO:7:

```
Ser  Pro  Pro  Phe  Glu  Asn  Ile  Asn  Leu  Tyr
1              5                        10
```

(2) INFORMATION FOR SEQ ID NO:8:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:8:

```
Gly  Gly  Gln  Pro  Leu  Trp  Ile  Thr  Ala  Thr  Lys
1              5                        10
```

(2) INFORMATION FOR SEQ ID NO:9:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO:9:

```
Val  Asn  Ser  Met  Gln  Thr  Val  Phe  Val  Gly  Tyr  Gly  Pro  Thr  Phe  Lys
1              5                        10                       15
```

(2) INFORMATION FOR SEQ ID NO:10:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:10:

```
Asp  Ile  Glu  His  Leu  Thr  Ser  Leu  Asp  Phe  Phe  Arg
1              5                        10
```

(2) INFORMATION FOR SEQ ID NO:11:

(i) SEQUENCE CHARACTERISTICS:
        (A) LENGTH: 23 amino acids
        (B) TYPE: amino acid
        (D) TOPOLOGY: linear (xi) SEQUENCE DESCRIPTION: SEQ ID NO:11:

```
Thr  Glu  Phe  Leu  Ser  Asn  Tyr  Leu  Thr  Asn  Val  Asp  Asp  Ile  Thr  Leu
1              5                        10                       15

Val  Pro  Gly  Thr  Leu  Gly  Arg
                20
```

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

GTTGGCAGCN ACRTGCCA                                                18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:13:

TGGCAYGTNG CTGCCAAC                                                                              18

( 2 ) INFORMATION FOR SEQ ID NO:14:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:14:

CTTGAAGGCA GGGTA                                                                                 15

( 2 ) INFORMATION FOR SEQ ID NO:15:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:15:

TAYCCTGCNT TYAAG                                                                                 15

( 2 ) INFORMATION FOR SEQ ID NO:16:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:16:

GGTNACYTCY TCAGG                                                                                 15

( 2 ) INFORMATION FOR SEQ ID NO:17:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:17:

CCTGARGARG TNACC                                                                                 15

( 2 ) INFORMATION FOR SEQ ID NO:18:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:18:

NGTNGCRTCR AATGGCACRT C                                                                          21

( 2 ) INFORMATION FOR SEQ ID NO:19:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:19:

GAYGTGCCAT TYGAYGCNAC N                                                                          21

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GTTDATRTTS TCRAATGGGG G         21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

CCCCCATTTG AGAACATCAA C         21

( 2 ) INFORMATION FOR SEQ ID NO:22:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CTTNGTNGCN GTDATCCANA RGGGYTGGCC GCC         33

( 2 ) INFORMATION FOR SEQ ID NO:23:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GGCGGCCARC CCYTNTGGAT HACNGCNACN AAG         33

( 2 ) INFORMATION FOR SEQ ID NO:24:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

CTTRAAGGTG GGGCCRTAGC CCACRAAGAC TGTYTGCAT         39

( 2 ) INFORMATION FOR SEQ ID NO:25:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

ATGCARACAG TCTTYGTGGG CTAYGGCCCC ACCTTYAAR         39

( 2 ) INFORMATION FOR SEQ ID NO:26:

( i ) SEQUENCE CHARACTERISTICS:
        ( A ) LENGTH: 9 amino acids (B) TYPE: amino acid
(C) STRANDEDNESS: single
(D) TOPOLOGY: linear (xi) SEQUENCE DESCRIPTION: SEQ ID NO:26:

Gln Tyr Leu His Gln Tyr Gly Ser Ser
1               5

(2) INFORMATION FOR SEQ ID NO:27:

(i) SEQUENCE CHARACTERISTICS:
    (A) LENGTH: 5 amino acids
    (B) TYPE: amino acid
    (C) STRANDEDNESS: single
    (D) TOPOLOGY: linear (xi) SEQUENCE DESCRIPTION: SEQ ID NO:27:

Val Leu Asn Tyr Phe
1               5

(2) INFORMATION FOR SEQ ID NO:28:

(i) SEQUENCE CHARACTERISTICS:
    (A) LENGTH: 5 amino acids
    (B) TYPE: amino acid
    (C) STRANDEDNESS: single
    (D) TOPOLOGY: linear (xi) SEQUENCE DESCRIPTION: SEQ ID NO:28:

Tyr Leu Asn Ala Thr
1               5

(2) INFORMATION FOR SEQ ID NO:29:

(i) SEQUENCE CHARACTERISTICS:
    (A) LENGTH: 11 amino acids
    (B) TYPE: amino acid
    (C) STRANDEDNESS: single
    (D) TOPOLOGY: linear (xi) SEQUENCE DESCRIPTION: SEQ ID NO:29:

His Leu Leu Tyr Gly Arg Pro Ala Val Leu Tyr
1               5                   10

(2) INFORMATION FOR SEQ ID NO:30:

(i) SEQUENCE CHARACTERISTICS:
    (A) LENGTH: 11 amino acids
    (B) TYPE: amino acid
    (C) STRANDEDNESS: single
    (D) TOPOLOGY: linear (xi) SEQUENCE DESCRIPTION: SEQ ID NO:30:

Ser Tyr Pro Glu Ile Leu Thr Pro Ala Asp Asn
1               5                   10

(2) INFORMATION FOR SEQ ID NO:31:

(i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:31:

Xaa Tyr Gly Phe Leu Phe Pro Pro Tyr Leu Ser Ser Ser Pro
1               5                   10

(2) INFORMATION FOR SEQ ID NO:32:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:32:

Thr  Phe  Pro  Asn  Leu  Tyr  Val  Xaa  Ala  Gln  Gly  Leu  Tyr  Trp  Ser
    1              5                        10                       15

( 2 ) INFORMATION FOR SEQ ID NO:33:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( x i ) SEQUENCE DESCRIPTION: SEQ ID NO:33:

Val  Asn  Val  Ile  Ser  Gly  Pro  Ile  Phe  Asp  Tyr  Asp  Tyr  Asp  Gly  Leu
    1              5                        10                       15

Xaa  Asp  Thr  Glu  Asp  Lys
               20

AUTOTAXIN: MOTILITY STIMULATING PROTEIN USEFUL IN CANCER DIAGNOSIS

BACKGROUND OF THE INVENTION

1. Field of the Invention

The present invention relates, in general, to a motility stimulating peptide and compositions comprising the same. In particular, the present invention relates to a purified form of the peptide, for example, autotaxin (ATX); a DNA segment encoding autotaxin; recombinant DNA molecules containing the DNA segment; cells containing the recombinant DNA molecule; a method of producing autotaxin; antibodies to autotaxin; and methods of cancer diagnosis and therapy using the above referenced peptides and DNA segments.

2. Background Information

Cell motility plays an important role in embryonic events, adult tissue remodeling, wound healing, angiogenesis, immune defense, and metastasis of tumor cells (Singer, S. J. and Kupfer, A. (1986) Ann. Rev. Cell Biol. 2, 337–365). In normal physiologic processes, motility is tightly regulated. On the other hand, tumor cell motility may be aberrantly regulated or autoregulated. Tumor cells can respond in a motile fashion to a variety of agents. These include host-derived factors such as scatter factor (Rosen, E. M. et al., (1989) In Vitro Cell Devel. Biol. 25, 163–173) and growth factors (Kahan, B. W. et al., (1987) Cancer Res. 47, 6324–6328; Stracke, M. L. et al., Biochem. Biophys. Res. Comm. 153, 1076–1083; Tamm, I., et al., (1989) J. Exp. Med. 170, 1649–1669; Wang, J. M., et al. (1990) Biochem. Biophys. Res. Comm. 169, 165–170; and Jouanneau, J., et al. (1991) Proc. Natl. Acad. Sci. USA 88, 2893–2897), components of the extracellular matrix (McCarthy, J. B., et al. (1984) J. Cell Biol. 98, 1474–1480), and tumor-secreted or autocrine factors (Liotta, L. A., et al. (1988) Cancer Surveys 7, 631–652; Ruff, M., et al. (1985) Clin. Immunol. Immunopath. 37, 387–396; Atnip, K. D., et al. (1987) Biochem. Biophys. Res. Comm. 146, 996–1002; Ohnishi, T., et al. (1990) J. Neurosurg. 73, 881–888; Silletti, S., et al. (1991) Cancer Res. 51, 3507–3511.; and Watanabe, H., et al. (1991) J. Biol. Chem. 266, 13442–13448).

Many types of host-derived soluble factors act in a paracrine fashion to stimulate cell locomotion. Motility-stimulating proteins called "scatter factors" have been identified which are produced by embryonic fibroblasts and by smooth muscle cells (Stoker, M., et al. (1987) Nature 327, 239–242). Scatter factors stimulate random and directed motility by epithelial cells, keratinocytes, vascular endothelial cells and carcinoma cells (Stoker, M., et al. (1987) Nature 327, 239–242; Rosen, E. M., et al. (1990) Proc. Soc. Exp. Biol. Med. 195, 34–43; and Weidner, K. M., et al. (1990) J. Cell. Biol. 111, 2097–2108), but not fibroblasts. In addition, a number of host-secreted growth factors have been demonstrated to stimulate motility in tumor cells, including nerve growth factor (Kahan, B. W., et al. (1987) Cancer Res. 47, 6324–6328) insulin-like growth factor-I (Stracke, M. L., et al. (1988) Biochem. Biophys. Res. Comm. 153, 1076–1083), interleukin-6 (Tamm, I., et al. (1989) J. Exp. Med. 170, 1649–1669), interleukin-8 (Wang, J. M., et al. (1990) Biochem. Biophys. Res. Comm. 169, 165–170), and acidic fibroblast growth factor (Jouanneau, J., et al. (1991) Proc. Natl. Acad. Sci. USA 88, 2893–2897). These paracrine factors may influence "homing" or the directionality of tumor cell motility.

In contrast to these host-derived factors, many types of tumor cells have been found to produce proteins termed "autocrine motility factors" which stimulate motility by the same tumor cells which make the factor (Liotta, L. A., et al. (1986) Proc. Natl. Acad. Sci. USA 83, 3302–3306). Autocrine motility factors are not specific for a given type of cancer cell but have a wide spectrum of activity on many types of cancer cells (Kohn, E. C., et al. (1990) Int. J. Cancer 46, 287–292), with little effect on normal fibroblasts or leukocytes.

Autocrine motility factors identified to date act through cell-surface receptors (Stracke, M. L., et al. (1987) Biochem. Biophys. Res. Comm. 147, 339–345; Nabi, I. R., et al. (1990) Cancer Res. 50, 409–414; Watanabe, H., et al. (1991) J. Biol. Chem. 266, 13442–13448) resulting in pseudopodial protrusion (Guirguis, R., et al. (1987) Nature 329, 261–263) leading to both random and directed migration (Liotta, L. A., et al. (1986) Proc. Natl. Acad. Sci. USA 83, 3302–3306; Atnip, K. D., et al. (1987) Biochem. Biophys. Res. Comm. 146, 996–1002; Ohnishi, T., et al. (1990) J. Neurosurg. 73, 881–888).

Prior studies of human A2058 melanoma cells have demonstrated that these cells are a particularly rich source of autocrine motility factors. An autocrine motility factor with a molecular mass of approximately 60 kDa has been previously isolated from the conditioned media of these cells. (Liotta, L. A., et al. (1986) Proc. Natl. Acad. Sci. USA 83, 3302–3306). Similar tumor cell derived or induced factors with the same molecular weight have subsequently been reported and purified by several investigators (Atnip, K. D., et al. (1987) Biochem. Biophys. Res. Comm. 146, 996–1002; Schnor, S. L., et al. (1988) J. Cell Sci. 90, 391–399; Ohnishi, T., et al. (1990) J. Neurosurg. 73, 881–888; Siletti, S., et al. (1991) Cancer Res. 51, 3507–3511; Watanabe, H., et al. (1990) J. Cell Biol. 111, 2097–2108). Such factors are thought to play a key role in tumor cell invasion.

Most of the motility factors identified to date have not been purified to homogeneity and have not been sequenced. The novel tumor motility factor of the present invention, named herein as autotaxin (ATX), has been purified and verified to be a homogeneous sample by 2-D gel electrophoresis. The protein of the present invention is unique from any previously identified or purified motility factor. The molecular size of ATX is about 125 kDa and it has an isoelectric point of approximately 7.7. ATX stimulates both random and directed migration of human A2058 melanoma cells at pM concentrations. The activity of this factor (ATX) is completely sensitive to inhibition by pertussis toxin. No significant homology has been found to exist between the protein of the invention and any mammalian protein including previous factors known to stimulate cell motility.

There is a great clinical need to predict the aggressiveness of a patient's individual tumor, to predict the local recurrence of treated tumors and to identify patients at high risk for development of invasive tumors. The present invention provides a functional marker which is functionally related to the invasive potential of human cancer. The invention further provides an assay for this secreted marker in body fluids, or in tissues. The assay of the invention can be used in the detection, diagnosis, and treatment of human malignancies and other inflamatory, fibrotic, infectious or healing disorders.

SUMMARY OF THE INVENTION

The present invention relates, generally, to a motility stimulating peptide and to a DNA segment encoding same.

It is a specific object of the present invention to provide the motility stimulating peptide, hereinafter referred to as autotaxin.

It is a further object of the present invention to provide a DNA segment that encodes autotaxin and a recombinant DNA molecule comprising same. It is a further object of the present invention to provide a cell that contains such a recombinant molecule and a method of producing autotaxin using that cell.

It is yet another object of the present invention to provide a method of purifying autotaxin.

Further objects and advantages of the present invention will be clear from the description that follows.

BRIEF DESCRIPTION OF THE DRAWINGS

FIG. 6A) 8–16% gradient gel of the first three purification steps, run under non-reducing conditions. Lane 2 is an aliquot of the pooled activity peak eluted from the phenyl sepharose fractionation. Lane 3 is an aliquot of the pooled activity peak eluted from the Con A affinity purification. Lanes 4 and 5 show the "peak" and "shoulder" of activity fractionated by weak anion exchange chromatography (FIG. 3). FIG. 6B) 7% gel of the activity peak fractionated by molecular sieve exclusion chromatography. Lanes 2 and 3 show the protein separation pattern of the total pooled activity peak when the gel was run under non-reducing and reducing conditions, respectively. FIG. 6C) 8–16% gradient gel of the final strong anionic exchange chromatographic separation, run under non-reducing conditions. Lane 2 comprises ~1% of the total pooled activity peak eluted from the column.

DETAILED DESCRIPTION OF THE INVENTION

Figure 1:
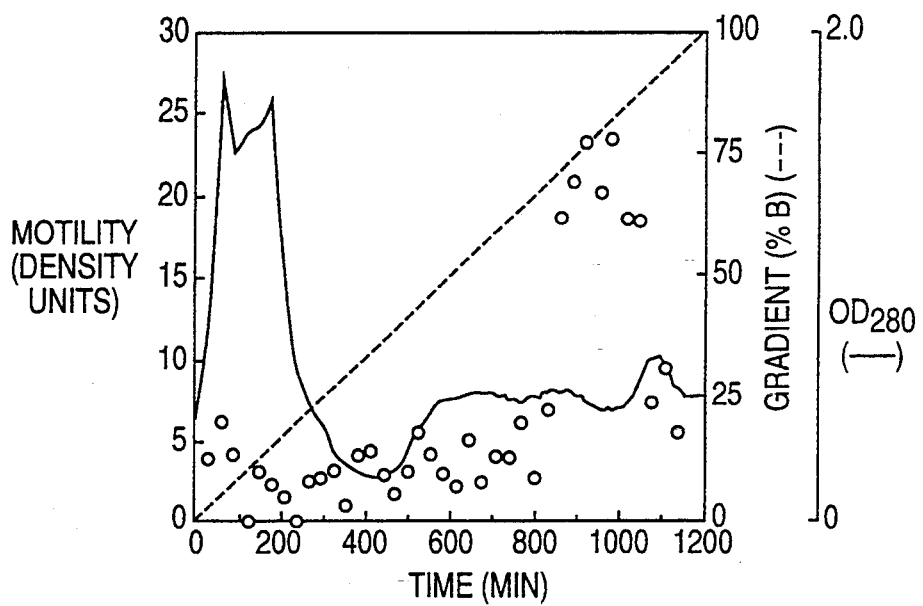
FIG. 1. Fractionation of ATX by hydrophobic interaction. A 200 ml sample of A2058 conditioned media was chromatographed on a 200 mL column of phenyl Sepharose-4B. Buffer A was 50 mM Tris (pH 7.5), 5% methanol, and 1.2 M ammonium sulfate. Buffer B was 50 mM Tris (pH 7.5), 5% methanol and 50% ethylene glycol. The gradient (----) represents a double linear gradient with decreasing ammonium sulfate (1.2 to 0.0M) and increasing ethylene glycol (0 to 50%). Absorbance was monitored at 280 nm (—) and indicated that most of the protein did not bind to the column. Ten ml fractions were assayed for motility stimulating capacity using the Boyden Chamber assay (o). The peak of motility activity occurred between 900 and 1050 minutes, ~12% of the gradient.

Autotaxin is secreted by A2058 human melanoma cells cultured in low abundance in serum-free conditioned medium. ATX is believed to be a glycosylated protein due to its high affinity for con A and amino acid sequence analysis of the ATX peptides. The molecular size of ATX is about 125 kDa as determined by SDS polyacrylamide gel electrophoresis under reducing conditions and it has an isoelectric point of 7.7±0.2. These characteristics distinguish ATX from several small growth factors and interleukins which are implicated in tumor cell motility (Stracke, M. L., et al. (1988) *Biochem. Biophys. Res. Comm.* 153, 1076–1083; Ruff, M., et al. (1985) *Clin. Immunol. Immunopatu.* 37, 387–396; Maciag, T., et al. (1984) *Sci.* 225, 932–935; Gospodarowicz, D. (1984) *Proc. Natl. Acad. Sci. USA* 81, 6963–6967; Van Snick, J. (1990) *Ann. Rev. Immunol.* 8, 253–278; Yoshimura, T. (1987) *Proc. Natl. Acad. Sci. USA* 84, 9233–9237).

The protein of the present invention, which in one embodiment is derived from A2058 human melanoma cells, can be prepared substantially free from proteins with which it is normally associated using, for example, the purification protocol disclosed herein. That protocol can be generally described as follows.

A large volume of serum-free conditioned medium from appropriate producer cells (e.g., tumor cells) is collected and concentrated approximately 500-fold. This concentrated conditioned medium is then separated from other contaminating proteins by techniques that rely on the chemical and physical characteristics of the protein. These include the molecular weight, relative hydrophobicity, net charge, isoelectric focusing point, and the presence of lectin-binding sugar residues on the protein.

Alternatively, the protein, or functional portion thereof, can be synthesized using chemical or recombinant means.

The protein of the present invention has a potent biological activity. The purified ATX is active in the picomolar range and 1 unit of activity corresponds to a concentration of approximately 500 pM as assessed by the cell motility assay described herein and elsewhere (Stracke, M. L., et al. (1989) *J. Biol. Chem.* 264, 21544–49).

The protein of the present invention has a molecular size, as determined by two dimensional gel electrophoresis, of from 120 to 130 kDa, or more specifically, about 125 kDa. Further the protein of the present invention can have a pI in the range of 7.5 to 7.9, preferably, approximately 7.7.

The present invention also relates to a DNA segment coding for a polypeptide comprising an amino acid sequence corresponding to ATX, or a unique portion of such a sequence (unique portion being defined herein as at least 5, 10, 25, or 50 amino acids). In one embodiment, the DNA segment encodes any one of the amino acid sequences shown in SEQ ID NO:1 to SEQ ID NO:11 and SEQ ID NO:26 to SEQ ID NO:33.

In another embodiment, the present invention relates to a recombinant DNA molecule comprising a vector (for example plasmid or viral vector) and a DNA segment coding for a polypeptide corresponding to ATX, as can be prepared by one skilled in the art. Preferably, the encoding segment is present in the vector operably linked to a promoter.

In a further embodiment, the present invention relates to a cell containing the above described recombinant DNA molecule. Suitable hosts cells include procaryotic cells (such as bacteria, including *E. coli*) and both lower eucaryotic cells (for example, yeast) and higher eucaryotic cells (for example, mammalian cells). Introduction of the recombinant molecule into the host cells can be effected using methods known in the art.

In another embodiment, the present invention relates to a method of producing a peptide having an amino acid sequence corresponding to ATX. The method comprises culturing the above described cell under conditions such that the DNA segment is expressed, and isolating ATX thereby produced.

In a further embodiment, the present invention relates to an antibody having affinity for autotaxin or peptide fragments thereof. The invention also relates to binding fragments of such antibodies. In one preferred embodiment, the antibodies are specific for autotaxin peptides having an amino acid sequence set forth in one of SEQ ID NO:1 through SEQ ID NO:11 and SEQ ID NO:26 through SEQ ID NO:33.

Antibodies can be raised to autotaxin or its fragment peptides, either naturally occurring or recombinantly produced, using methods known in the art.

ATX peptide fragments described above can be joined to other materials, particularly polypeptides, as fused or covalently joined polypeptides to be used as carrier proteins. ATX and its fragments can be fused or covalently linked to a variety of carrier proteins, such as keyhole limpet hemocyanin, bovine serum albumin, tetanus toxoid, etc. See for example, *Microbiology*, Hoeber Medical Division (Harper and Row, 1969), Landsteiner, Specificity of Serological Reactions (Dover Publications, New York, 1962) and Williams et al., *Methods in Immunology and Immunochemistry*, Vol. 1 (Academic Press, New York, 1967), for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts. Description of techniques for preparing such monoclonal antibodies may be found in Stites et al., editors, *Basic and Clinical immunology*, (Lange Medical Publications, Los Altos, Calif., Fourth edition) and references cited therein, and in particular in Kohler and Milstein in *Nature* 256:495–497 (1975), which discusses one method of generating monoclonal antibodies.

In another embodiment, the present invention relates to an oligonucleotide probe synthesized according to the sense or antisense degenerative sequence set forth in one of SEQ ID NO:1 through SEQ ID NO:11 and SEQ ID NO:26 through SEQ ID NO:33.

No significant homologies to known proteins found upon comparing the sequences set forth in SEQ ID NO:1 through SEQ ID NO:11 and SEQ ID NO:26 through SEQ ID NO:33 with those in the following protein databases: GenBank (68.0), EMBL (27.0), SWISS-PROT (18.0), and GenPept (64.3). Thus, autotaxin is a unique, previously undescribed protein.

In a further embodiment, the present invention relates to a method of diagnosing cancer metastasis and to a kit suitable for use in such a method. Preferrably, antibodies to ATX can be used in, but not limited to, ELISA, RIA or immunoblots configurations to detect the presence of ATX in body fluids of patients (e.g. serum, urine, pleural effusions, etc.). These antibodies can also be used in immunostains of patient samples to detect the presence of ATX.

In yet another embodiment, the present invention relates to in vivo and in vitro diagnostics. ATX may be radiolabelled, by means known to one skilled in the art, and injected in cancer patients with appropriate ancillary substances also known to one skilled in the art, in order to ultimately detect distant metastatic sites by appropriate imagery. The level of ATX in tissue or body fluids can be used to predict disease outcomes and/or choice of therapy which may also include ATX inhibitors.

In a further embodiment, the present invention relates to a treatment of cancer. ATX antibodies can be cross-linked to toxins (e.g., Ricin A), by means known to one skilled in the art, wherein the cross-linked complex is administered to cancer patients with appropriate ancillary agents by means known to one skilled in the art, so that when the antibody complex binds to the cancer cell, the cell is killed by the cross-linked toxin.

The present invention is described in further detail in the following non-limiting examples.

EXAMPLES

The following protocols and experimental details are referenced in the Examples that follow:

Materials. The polycarbonate Nuclepore membranes and the 48-well microchemotaxis chambers were obtained from Neuro Probe, Inc. Pertussis toxin (PT), ethylene glycol (biotechnology grade), methyl α-D-mannopyranoside were obtained from commercial vendors. The ampholyte, pH 3–10 Bio-Lyte and pH 8–10 Bio-Lyte, were obtained from Bio-Rad. Phenyl Sepharose CL-4B; affi-Gel concanavalin A; ZORBAX BioSeries-WAX (weak anion exchange) column (9.4 mm×24 cm); Spherogel-TSK 4000SW, 3000SW and 2000SW columns (each 7.5 mm×30 cm); the Pro-Pac PA1 (4×50 mm) strong anion exchange column; the Aquapore RP300 C-8 reverse phase column (220×2.1 mm); and the AminoQuant C-18 reverse phase column (200×2.1 mm) were also obtained from commercial sources.

Cell Culture. The human melanoma cell line A2058, originally isolated by Todaro (Todaro, G. J., et al. (1980) Proc. Natl. Acad. Sci, USA 77, 5258–5262), was maintained as previously described by Liotta (Liotta, L. A., et al. (1986) Proc. Natl. Acad. Sci, USA 83, 3302–3306).

Production of Autotaxin. A2058 cells were grown up in T-150 flasks, trypsinized, and seeded into 24,000 cm² cell factories at a cell density of $1 \times 10^{10}$ cells/factory. After 5–6 days, the serum-containing medium was removed and the cells were washed with DPBS. The factories were maintained in DMEM without phenol red, supplemented with 4 mM glutamine, 100 units/ml penicillin, 100 μg/ml streptomycin, 5 μg/ml crystallized bovine serum albumin, 10 μg/ml bovine insulin, and 1 μM aprotinin. Culture supernatants were harvested every 3 days, frozen at −40° C. and replaced with fresh serum-free medium. Each cycle of supernatant was tested for ATX production with a cell motility assay detailed below. Typically, a cell factory continued to be productive for 9–11 of these cycles.

After accumulation of approximately 45–60 L of supernatant, the culture supernatants were thawed and concentrated down to 2–2.5 L using an Amicon S10Y30 spiral membrane ultrafiltration cartridge. This supernatant was further concentrated in an Amicon high performance ultrafiltration cell using Diaflo membranes. The final volume achieved from 100–200 L of conditioned medium was typically 250–400 ml. All ultrafiltrations were performed at 4° C.

Cell Motility Assays. Purification of autotaxin was monitored by testing the motility-stimulating capacity of the fractions collected from the columns. These fractions were in buffers unsuitable for a chemotaxis assay so each fraction had to be washed into an appropriate buffer, i.e., 0.1% (w/v) BSA in DPBS containing calcium and magnesium. This dialysis was performed by adding aliquots of each fraction to be tested into Centricon-30 ultrafiltration tubes, which retain molecular species larger than 30,000 daltons.

The assay to determine motility was performed in triplicate using a 48-well microchemotaxis chamber as described elsewhere in detail (Stracke, M. L., et al. (1987) Biochem. Biophys. Res. Comm. 146, 339–345; Stracke, et al. (1989) J. Biol. Chem. 264, 21544–21549). The Nuclepore membranes used in these modified Boyden chambers were fixed and stained with Diff-Quik. Chemotaxis was quantitated either by reading the stained membranes with a 2202 Ultroscan laser densitometer or by counting 5 randomly chosen high power fields (HPF) under light microscopy (400×) for each replicate. Densitometer units (wavelength - 633 nm) have been shown to be linearly related to the number of cells per HPF (Taraboletti, G., (1987) J. Cell Biol. 105, 2409–2415; Stracke, M. L., et al. (1989) J. Biol. Chem. 264, 21544–21549). Typically, unstimulated motility (background) corresponded to 5–10 cells/HPF and highly responding cells to 70–100 cells/HPF above unstimulated background (i.e., 75–110 total cells/HPF).

For experiments using PT, the toxin was pre-incubated with the cells for 1–2 hr. at room temperature prior to the assay and maintained with the cells throughout the assay (Stracke, M. L., et al. (1987) Biochem. Biophys. Res. Comm. 146, 339–345). The treated cells were tested for their motility response to the chemoattractant as well as for unstimulated random motility.

Purification of Autotaxin. Ammonium sulfate, to a final concentration of 1.2M, was added to the concentrated A2058 conditioned medium for 1 hr. at 4° C. The solution was spun in a RC2-B Ultraspeed Sorvall centrifuge at 10,000×g for 15 min. Only the supernatant had the capacity to stimulate motility.

In the first step, the sample was fractionated by hydrophobic interaction chromatography using 200 ml phenyl Sepharose CL-4B column equilibrated into 50 mM Tris (pH 7.5), 5% (v/v) methanol and 1.2M ammonium sulfate. The supernatant from the ammonium sulfate fractionation was added to this column and eluted using linear gradients of 50 mM Tris (pH 7.5), 5% (v/v) methanol, with decreasing (1.2–0.0) M ammonium sulfate and increasing (0–50) % (v/v) ethylene glycol at 1 ml/min.

The active peak was pooled, dialyzed into 50 mM Tris, 0.1M NaCl, 0.01M $CaCl_2$, 20% (v/v) ethylene glycol, and subjected to a second fractionation by lectin affinity chromatography using a 40 ml Affi-Gel concanavalin A column run at 1 ml/min. The sample was eluted in a stepwise fashion in the same buffer with 0, 10, and 500 mM methyl α-mannopyranoside added successively. Fractions from each step of the gradient were pooled and tested for their capacity to stimulate motility.

In the third purification step, the sample that eluted at 500 mM α-methyl-mannopyranoside was dialyzed into 10 mM Tris (pH 7.5) with 30% (v/v) ethylene glycol and fractionated by weak anion exchange chromatography. Chromatography was carried out on a ZORBAX BioSeries-WAX column using a Shimadzu BioLiquid chromatograph and eluted with a linear gradient of (0.0–0.4M) sodium chloride at 3 ml/min.

The active peak was pooled, dialyzed against 0.1M sodium phosphate (pH 7.2), 10% (v/v) methanol, and 10% (v/v) ethylene glycol, and subjected to a fourth fractionation step on a series of Spherigel TSK columns (4000SW, 4000SW, 3000SW, 2000SW, in that order). This molecular sieve step was run using the Shimadzu BioLiquid chromatograph at 0.4 ml/min.

The active peak was pooled and dialyzed into 10 mM Tris (pH 7.5), 5% (v/v) methanol, 20% (v/v) ethylene glycol and subjected to a fifth (strong anion exchange) chromatography step, a Pro-Pac PA1 column run at 1 ml/min using a Dionex BioLC with AI450 software. The sample was eluted with a linear gradient of (0.0–0.4M) NaCl.

In order to calculate activity yields after each step of purification, a unit of activity had to be derived. The dilution curve of autotaxin was biphasic with a broad peak and a linear range at sub-optimal concentrations. One unit of activity/well (i.e., 40 units/ml) was defined as 50% of the maximal activity in a full dilution curve. This allowed calculation of the activity contained in any volume from the dilution needed to achieve 1 unit/well. Therefore, if a 1:10 dilution were needed in order to produce 1 unit of activity/well, the material contained 10×40=400 units/mi.

Gel Electrophoresis. Protein samples were analyzed by SDS-polyacrylamide gel electrophoresis using the conditions of Laemmli (Laemmli U. K. (1970) *Nature* 227, 680–685). In brief, 7 or 8% SDS-containing polyacrylamide gels were prepared or pre-poured (8–16%) gradient gels were obtained commercially. Samples were prepared with or without reducing conditions (5% β-mercaptoethanol). After electrophoretic separation, the gels were stained using Coomassie Blue G-250 as previously described (Neuhoff, V., et al. (1988) *Electrophoresis* 9, 255–262). In this staining protocol, which ordinarily requires no destaining step, the Coomassie stain appears to be able to stain as little as 10 ng of protein.

For two-dimensional electrophoresis, the protein, in 20% ethylene glycol, was dried in a Speed-vac and redissolved in loading solution: 9M urea, 1% (v/v) pH 3–10 Bio-Lyte, and 2.5% (v/v) Nonidet P40. This sample was then subjected to isoelectric focusing (O'Farrell, P. H. (1975) *J. Biol. Chem.* 250, 4007–4021) using a Bio-Rad tube cell in 120×3 mm polyacrylamide tube gels containing 9M urea, 2% (v/v) pH 3–10 Bio-Lyte, 0.25% (v/v) pH 8–10 Bio-Lyte and 2.5% (v/v) Nonidet-P40. Reservoir solutions were 0.01M phosphoric acid and 0.02M NaOH. Non-equilibrium isoelectric focusing (O'Farrell, P. H., et al. (1977) *Cell* 12, 1133–1142) was run initially with constant voltage (500 v) for 5 hr. Since the protein was basic, the procedure was repeated under equilibrium conditions (500 v for 17 hr.). Electrophoresis in the second dimension was performed on a 7.5% polyacrylamide using the conditions of Laemmli (1970). The gel was stained with Coomassie Blue G-250 as above.

Preparation of peptides for internal sequence of autotaxin. Homogeneous ATX was sequentially digested with cyanogen bromide and, following reduction and pyridylethylation, with trypsin (Stone, M, et al. (1989) in *A Practical Guide to Protein and Peptide Purification for Microsequencing* Matsudaira, P. T., ed.) pgs. 33–47, Academic Press, N.Y.). The resulting fragments were then separated by gradient elution on an Aquapore RP300 C-8 reverse phase column: 0.1% (v/v) trifluoroacetic acid and (0–70) % acetonitrile over 85 min. at a flow rate of 0.2 ml/min. A Dionex AI450 BioLC system was utilized and fractions were collected by hand while monitoring the absorbance at 215 nm.

Sequence analysis of peptides. The amino acid sequences of peptides resulting from digestion and purification of ATX peptides #1–7 and 12–18, corresponding to SEQ ID NO:1 through SEQ ID NO:7 and SEQ ID NO:26 through SEQ ID NO:32, respectively, were determined on a Porton Instruments 2020 off-line sequenator using standard program #1. Phenylthiohydantoin amino acid analysis of sequenator runs were performed on a Beckman System Gold HPLC using a modified sodium acetate gradient program and a Hewlett-Packard C-18 column. ATX-100 (SEQ ID NO:8), ATX-101 (SEQ ID NO:9), ATX-102 (SEQ ID NO:10), ATX-103 (SEQ ID NO:11) and ATX 104 (SEQ ID NO:33) were sequenced from gel-purified ATX.

Protein databases (Pearson, W. R., et al. (1988) *Proc. Natl. Acad. Sci.* USA 85, 2444–2448) that were searched for homologies in amino acid sequence with the ATX peptides include: GenBank (68.0), EMBL (27.0), SWISS-PROT (18.0), and GenPept (64.3).

EXAMPLE 1

Purification of Autotaxin

The A2058 cells had been previously shown to produce protein factors which stimulate motility in an autocrine fashion (Liotta, L. A., et al. (1986) *Proc. Natl. Acad. Sci.* USA 83, 3302–3306). Conditioned medium from these cells was therefore used to identify and purify a new motility-stimulating factor, which is here named autotaxin. Since the purification was monitored with a biological assay, motility-stimulating activity had to be maintained throughout. The activity proved to be labile to freezing, acidic buffers, proteases (but not DNase or RNase), reduction, strong chaotrophic agents (e.g. >4M urea), and a variety of organic solvents (isopropanol, ethanol, acetonitrile). An organic solvent, ethylene glycol, which did not decrease bioactivity, was added for both storage and chromatographic separation.

100–200 L of serum-free conditioned medium were required in order to produce enough autotaxin for amino acid sequence analysis. The medium contained low concentrations of both BSA (5 μg/ml) which was needed as a carrier protein and insulin (10 μg/ml) which was required to support cell growth in low protein medium. Ultrafiltration to concentrate this large volume was performed with low protein-binding YM30 membranes which retain molecular species with $M_r > 30,000$. As seen in Table 1, 200 L of conditioned medium prepared in this manner resulted in $10 \times 10^6$ units of activity. However, the initial unfractionated conditioned medium contained additional substances known to stimulate activity, particularly insulin, which does not completely wash out in the ultrafiltration step and which is additive to the motility stimulating activity in a complex manner (Stracke, M. L., et al. (1989) *J. Biol. Chem.* 264, 21544–21549). This had to be taken into account in order to determine yields for subsequent steps in which insulin had been removed.

mM sugar. Consequently, a step gradient was used to elute. Pure BSA failed to bind to con A.

Activity was found primarily in the 500 mM step of methyl α-D-mannopyranoside. There appeared to be no significant loss of activity as seen in Table 1; however, specific activity (activity/mg total protein) increased thirty-fold. Gel electrophoresis of the pooled and concentrated peak (FIG. 6A, column 3) revealed that the BSA overload was no longer apparent and the number of bands were much reduced. When the unbound protein was concentrated and applied to a gel, it appeared identical to the active peak from phenyl Sepharose-4B with a large BSA band.

Figure 3:
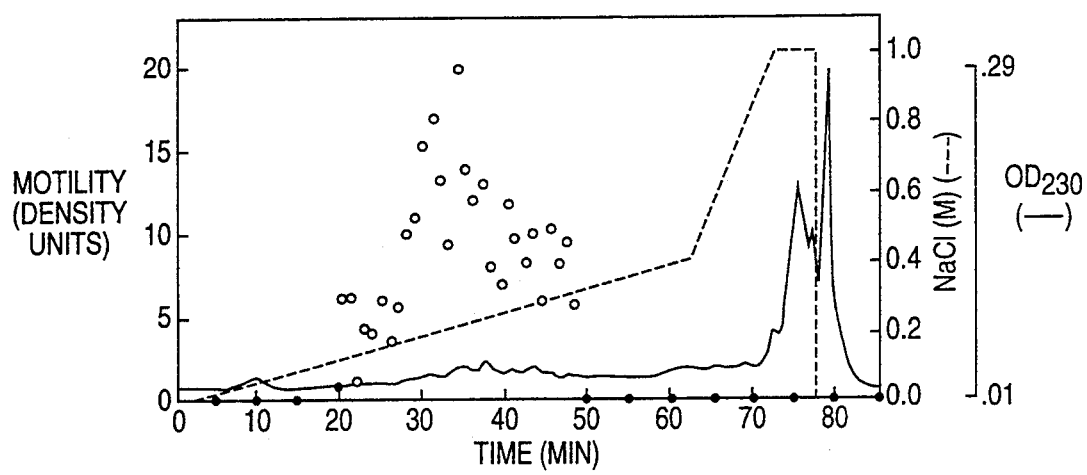
FIG. 3. Purification of ATX by weak anionic exchange chromatography. Approximately 30% of the activity peak eluted from the Con A affinity column was applied to a ZORBAX BioSeries-WAX column. The bound components were eluted with an NaCl gradient (----) in a buffer consisting of 10 mM Tris (pH 7.5) and 30% ethylene glycol. Motility (o) was assayed in 1.0 ml fractions. The peak of activity eluted in a discrete but broad region in the shallow portion of the gradient. Absorbance was monitored at 230 nm (_). The majority of the protein components not associated with activity bound strongly to the column were eluted at 1.0M NaCl. One of two chromatographic runs is shown.

The third purification step involved fractionating the previous active peak by weak anion exchange chromatography as shown in FIG. 3. Under the running conditions, activity eluted in a broad peak-shoulder or double peak in the middle of the shallow portion (0.0–0.4M) of the NaCl gradient. The largest proportion of protein, lacking in motility-stimulating capacity, bound strongly to the column and eluted off in high salt (1M NaCl). There appeared to be no significant loss of activity, though specific activity increased by twenty-fold

TABLE 1

PURIFICATION OF AUTOTAXIN

| Purification Step | Protein (mg) | Activity[a] (total units) | Specific Activity (units/mg) | Recovery (%)[b] |
|---|---|---|---|---|
| 200 L Conditioned Medium | 33,000 | 10,000,000[c] | 300 | |
| Phenyl Sepharose | 1,235 | 460,000 | 370 | 100 |
| Concanavalin A | 58 | 660,000 | 11,400 | 100 |
| Weak Anion Exchange | 4.5 | 490,000 | 110,000 | 100 |
| TSK Molecular Sieves | ~0.4[d] | 220,000 | 550,000 | 48 |
| Strong Anion Exchange | ~0.04[d] | 24,000[e] | 600,000 | 5.2 |

[a]Activity calculated from Boyden chamber assay. The dilution which resulted in 50% of maximal activity (generally approximately 20 laser density units or ~40 cells/HPF) was chosen to have 1 unit of activity per well (equivalent to 40 units/ml).
[b]Recovery was estimated from activity, after the first purification column (i.e., phenyl sepharose).
[c]Initial activity in the unfractionated conditioned medium reflected the fact that insulin was used in the medium as a necessary growth factor under low protein conditions.
[d]Estimated protein is based on quantification by amino acid analysis.
[e]This specific activity for purified protein corresponds to ~10 fmol ATX/unit of motility activity (in a Boyden chamber well).

The first step in the purification involved fractionation by hydrophobic interaction chromatography using a phenyl Sepharose CL-4B column. The results are shown in FIG. 1. Most proteins, including insulin, eluted from the column in early fractions or in the void. However, the peak of activity eluted relatively late. The activity which was purified was estimated as 460,000 units ±20% (Table 1). As the pooled peak of activity from the phenyl Sepharose fractionation is considered to be the first sample without significant insulin contamination, subsequent yields are measured against its total activity. Gel electrophoresis of a small portion of the pooled peak of activity (FIG. 6A, column 2) revealed a large number of protein bands with BSA predominant from the original conditioned medium.

Figure 2:
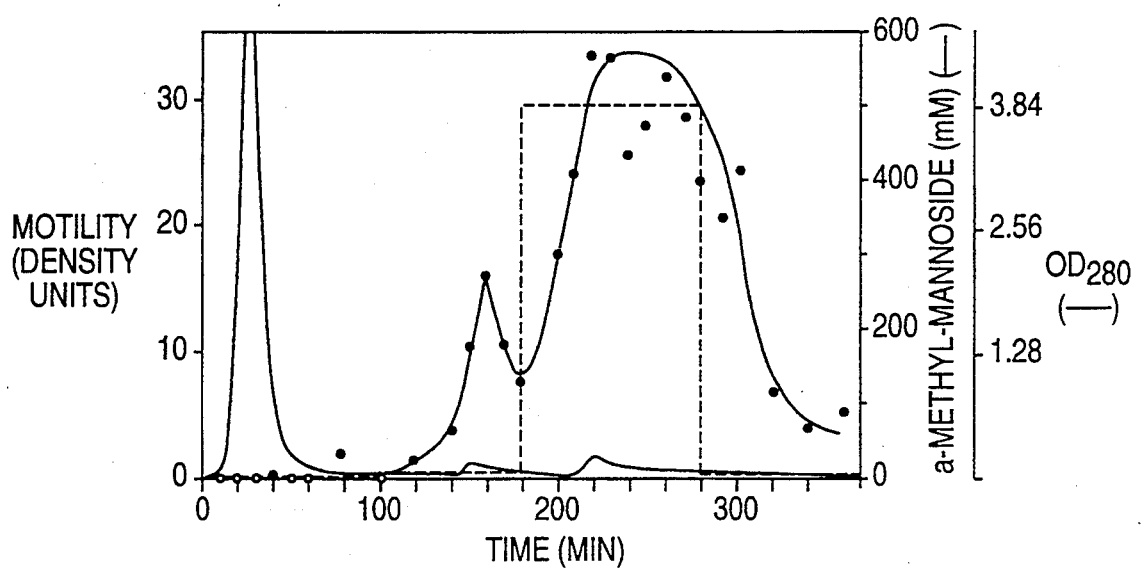
FIG. 2. Isolation of ATX by lectin affinity chromatography. 20 ml portions of the phenyl Sepharose activity peak were affinity purified on a 40 ml Concanavalin A Affi-Gel column. The bound components were eluted with a step gradient (----) of methyl α-D-mannopyranoside (0.0 mM, 10 mM, and 500 mM) in a buffer consisting of 0.05M Tris (pH 7.5), 0.1M NaCl, 0.01M $CaCl_2$ and 20% ethylene glycol. Absorbance was monitored at 280 nm (_) and indicated that the majority of the protein components did not bind to the column. Motility was assayed in 10 mL fractions (...o...) and was found predominantly in the 500 mM elution concentration. One of seven chromatographic runs is shown.

In the second step of purification, the active peak was applied to the lectin affinity column, Affi-Gel concanavalin A. As shown in FIG. 2, most protein (estimated to be 90% of the total absorbance at 280 nm) failed to bind to the column at all. The non-binding fraction contained essentially no motility-stimulating activity (see dotted line in FIG. 2). When a linear gradient of methyl α-D-mannopyranoside was applied to the column, chemotactic activity eluted off in a prolonged zone, beginning at a concentration of approximately 20

Figure 6C:
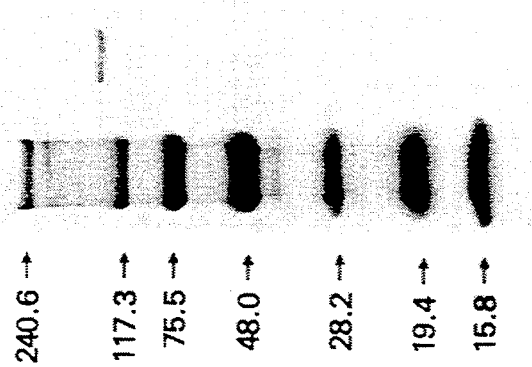
FIGS. 6A, 6B and 6C. Protein components associated with the activity peaks from various stages of purification. The activity peak from each chromatographic fractionation was pooled, concentrated and analyzed by SDS-polyacrylamide gel electrophoresis. Molecular weight standards are in Lane 1 for each panel.
Figure 6B:
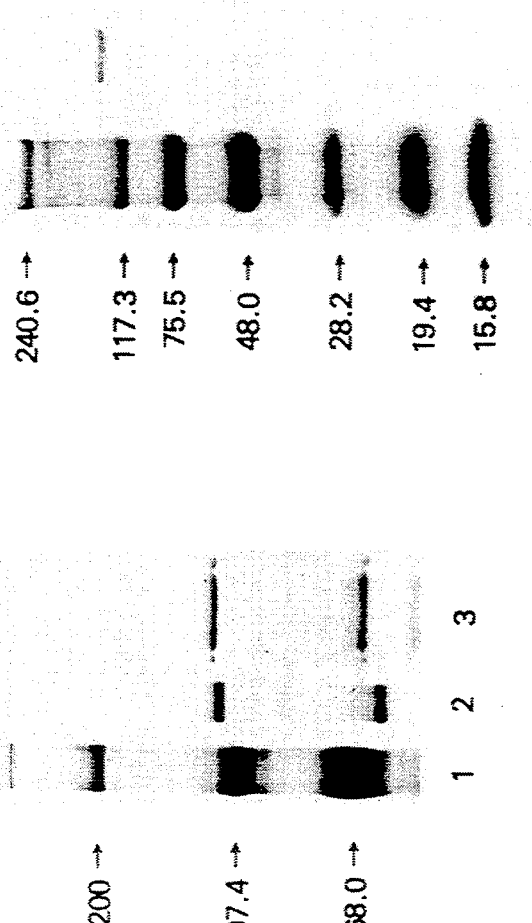
Figure 6A:
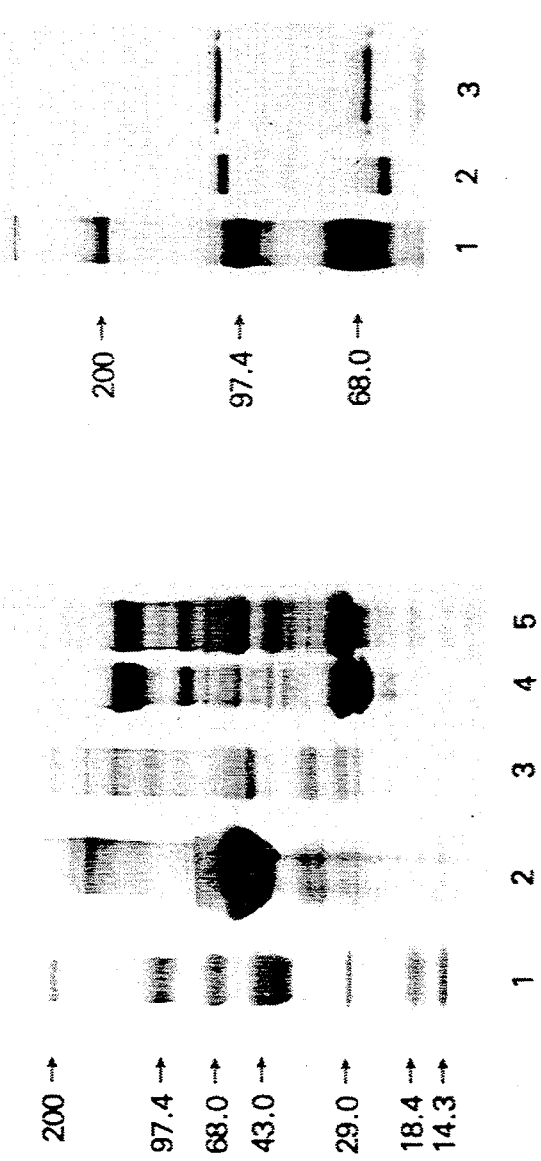

(Table 1). Analysis by gel electrophoresis of both the peak (28–34 min. in FIG. 3) and the shoulder (35–45 min. in FIG. 3) is shown in FIG. 6A (columns 4 and 5, respectively). Two predominant protein bands resulted: a broad doublet around 25–35 kDa and a second doublet around 110–130 kDa.

Figure 4:
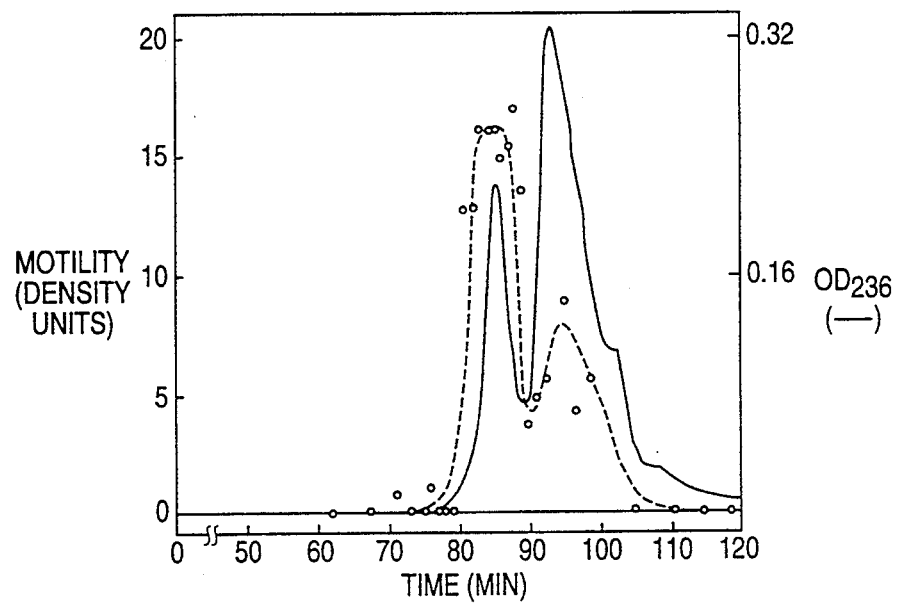
FIG. 4. Purification of ATX by molecular sieve exclusion chromatography. The entire activity peak eluted from the weak anion exchange column was applied to a series of TSK columns (4000SW, 4000SW, 3000SW, and 2000SW, in this order). Proteins were eluted in a buffer consisting of 0.1M $NAPO_4$ (pH 7.2) with 10% methanol and 10% ethylene glycol. Two major protein peaks were evident by monitoring the absorbance at 235 nm (_). Motility (...o...) was assayed in 0.4 ml samples and found predominantly in the first, smaller, protein peak.

In the fourth purification step, the active peak was applied to a series of molecular sieves. Spectrophotometric monitoring of the eluant revealed two large peaks of protein (FIG. 4). Activity corresponded to the first, higher molecular weight peak. Recovery of activity was ~48% with a five-fold increase in specific activity. Analysis by gel electrophoresis was performed under non-reducing and reducing conditions as shown in FIG. 6B (columns 2 and 3, respectively). This fractionation step had essentially removed all contaminating protein of molecular weight <55 kDa. The predominant band remaining has a molecular weight of 120 kDa unreduced and 125 kDa reduced; there are two minor bands with molecular weights 85 kDa and 60 kDa. The fact that the 120 kDa protein changes so little in electrophoretic mobility after reduction would tend to indicate a paucity of disulfide bonds. However, the existing disulfide bonds have functional significance because motility-stimulating activity is labile to reduction.

Figure 5:
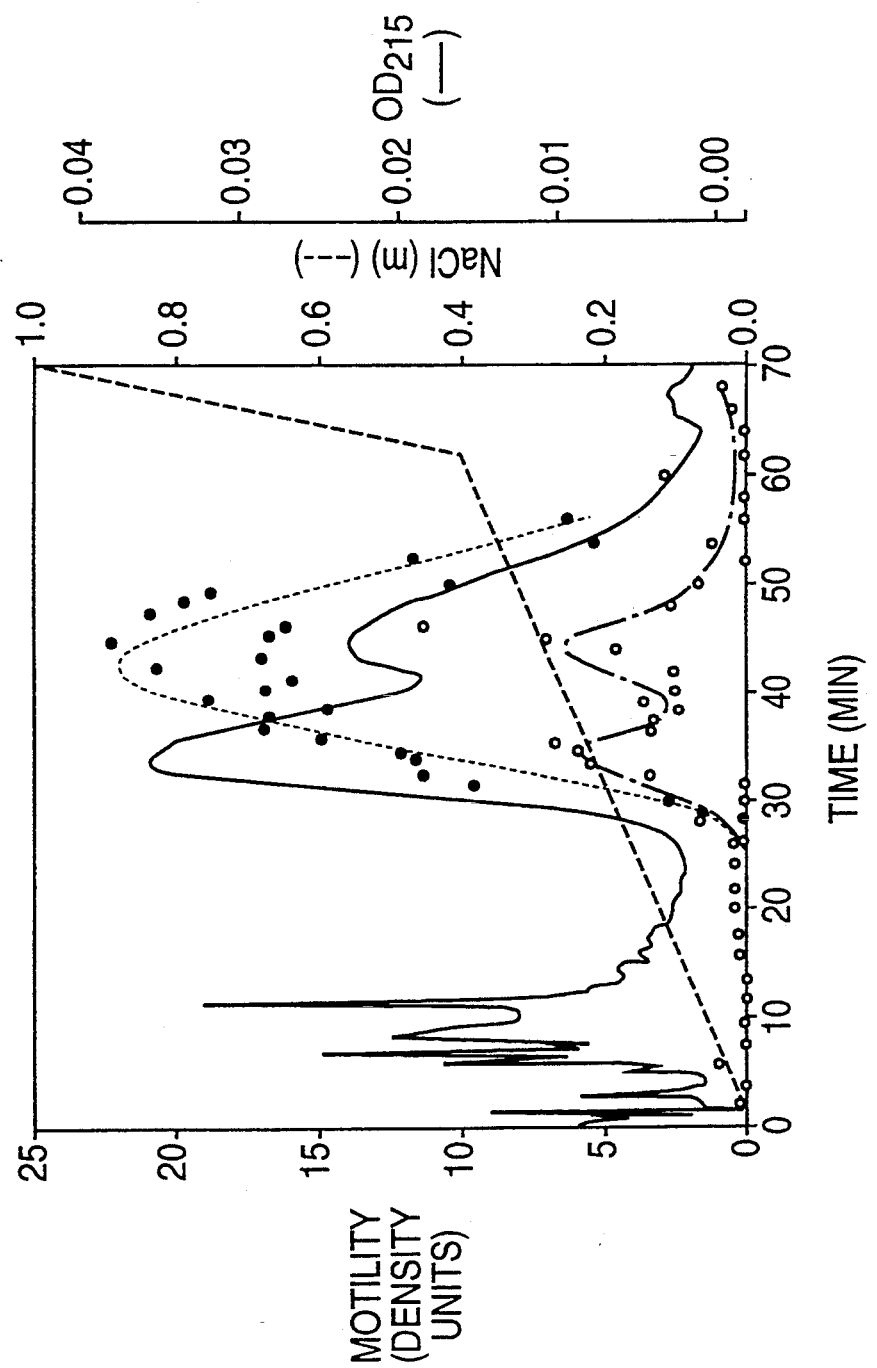
FIG. 5. Final purification of ATX by strong anionic exchange chromatography. Approximately 15% of the activity peak from the molecular sieve exclusion series was applied to a Pro-Pac PA1 column. Protein which bound to the column was eluted with a NaCl gradient (----) in a buffer consisting of 10 mM Tris (pH 7.5), 5% methanol and 20% ethylene glycol. Absorbance was monitored at 215 nM (_). Motility activity was assayed in 1.0 ml fractions at two different dilutions: 1/5 (...o....) or 1/15 (._.o._.). Activity was found to correspond to a double protein peak in the central region of the gradient.

The fifth purification step involved fractionation of the active peak by strong anion exchange chromatography. As shown in FIG. 5, activity corresponds to two broad optical absorbance peaks in the middle of the gradient with contaminating proteins eluting earlier. These two peaks were identical by amino acid analysis and by polyacrylamide gel electrophoretic separation. They presumably represent different glycosylation states of the same parent protein. Activity is shown in FIG. 5 at two different sample dilutions. Several dilutions of the fractionated samples were often necessary in order to resolve the true "peak" of activity as the shape of the ATX dilution curve was not sharp due to saturation and down regulation at high concentrations. Recovery from this chromatographic step is lower (5% compared to phenyl Sepharose), as might be expected when a minute quantity of protein is applied to a column; however, specific activity again increased (Table 1). Analysis by gel electrophoresis revealed a single protein band at molecular weight 120 kDa, unreduced (FIG. 6C, column 2).

EXAMPLE 2

Characterization of Autotaxin

Figure 7:
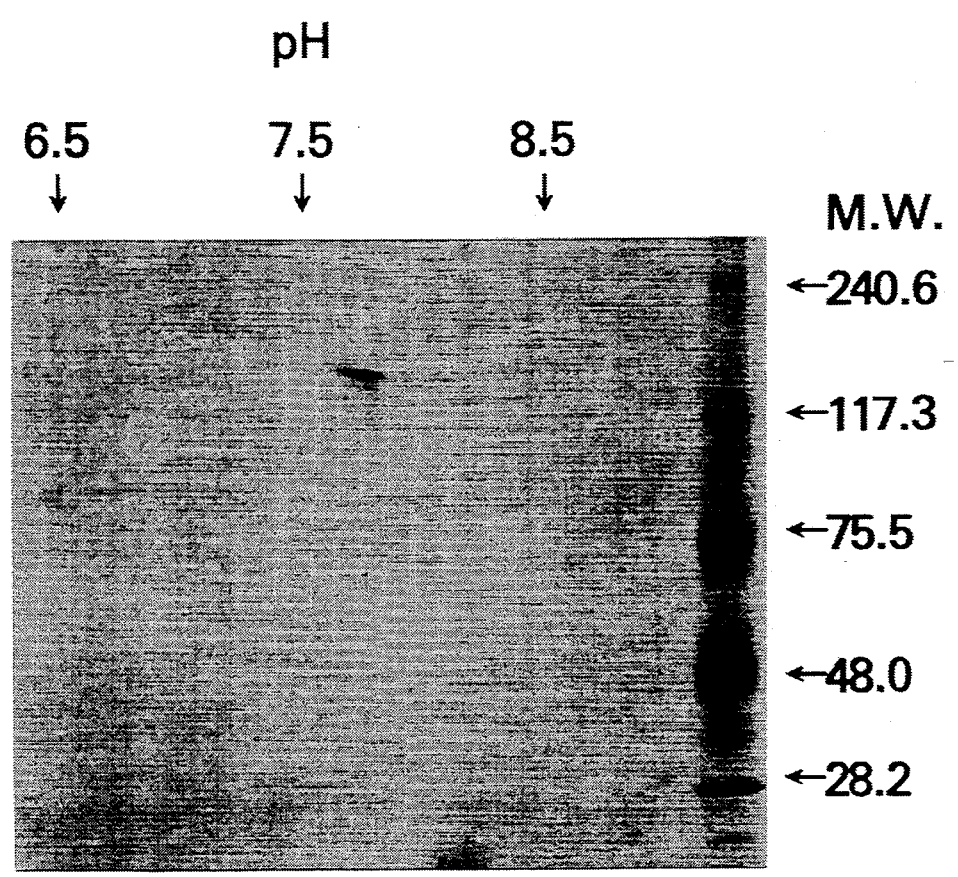
FIG. 7. 2-dimensional gel electrophoresis of ATX. Purified ATX (FIG. 6, Panel C) was subjected to nonequilibrium isoelectric focusing (5 hr. at 500 v), then applied to a 7.5% SDS-polyacrylamide gel for the second dimension. The pH separation which resulted was measured in 0.5 cm samples of concurrently run tube gels and is shown at the top. Molecular weight standards for the second dimension are shown on the right. This analysis reveals a single component with $pI = 7.7 \pm 0.2$ and $M_r = 120,000$.

Two dimensional gel electrophoresis of the purified protein (FIG. 7) revealed a single predominant band. The band slopes downward slightly toward the basic side of the gel in a manner that is characteristic of glycosylated proteins. A basic pI of 7.7±0.2 was essentially the same whether the isoelectric focusing was run under non-equilibrium conditions (5 hr.) or was allowed to go to equilibrium (17 hr.).

Figure 8:
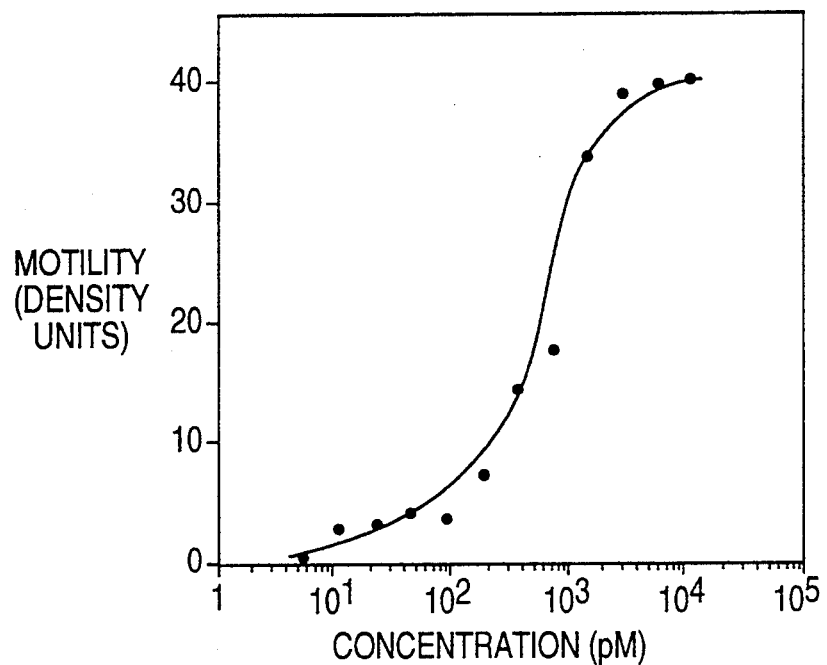
FIG. 8. Dilution curve of ATX. Purified ATX (FIG. 6, Panel C) was serially diluted and tested for motility-stimulating activity. The result, with unstimulated background motility subtracted out, shows that activity is half-maximal at ~500 pM ATX.
Figure 9:
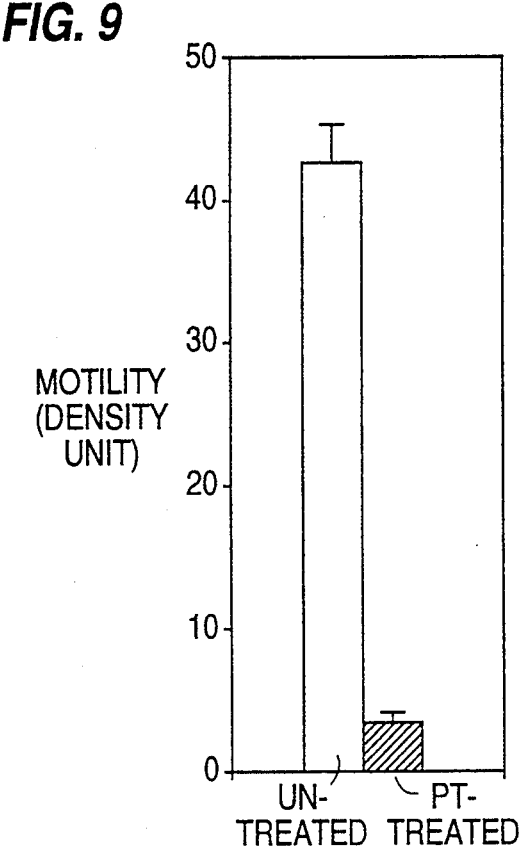
FIG. 9. Pertussis toxin (PT) sensitivity of ATX. A2058 cells were pre-treated for 1 hr. prior to the start of the motility assay with 0.5 μg/ml PT in 0.1% BSA-DMEM or with 0.1% BSA-DMEM alone (for untreated control). The motility activity stimulated by purified ATX (FIG. 6, Panel C) was then assessed for the two treatment groups. The result, expressed as cells/HPF±S.E.M. with unstimulated background motility subtracted out, reveals profound inhibition of PT-treated cells (hatched) compared to untreated cells (solid). PT had no effect on cell viability. S.E.M.'s were <10%.

A dilution curve of the purified protein is shown in FIG. 8. The protein is active in the pM range and 1 unit of activity appears to correspond to a concentration of 400–600 pMolar (or approximately 10 fmol of autotaxin/Boyden chamber well). When dilutions were begun at higher concentrations of ATX, the resultant curve showed a broad plateau with down regulation at the highest concentrations. The motility response to purified autotaxin is highly sensitive to pertussis toxin (Table 2 and FIG. 9) with approximately 95% inhibition of activity at 0.5 µg/ml PT.

TABLE 2

| Effect of Pertussis Toxin (PT) on Autotaxin-stimulated motility A2058 Motility Response (density units[1]) | | |
|---|---|---|
| | control cells[2] | Pertussis toxin-treated cells[3] |
| Condition medium[4] | 60.3 | 0.4 |
| Purified Autotaxin | 38.5 | 0.0 |

[1]Chemotaxis quantitated by motility assay (Stracke, M. L., et al. (1978) Biochem. Bioshys. Res. Comm. 146, 339–345)
[2]A2058 cell suspended at 2 × 10⁶ cells/ml in DMEM supplemented with 1 mg/ml bovine serum and rocked at room temperature for 1 hr.
[3]As control with 0.5 µg/ml pertussis toxin.
[4]Prepared by adding DMEM without phenol red supplemented with 0.1 mg/ml bovine serum albumin to subconfluent flasks of A2058 cells. The medium was harvested after 2 days incubation at 37° C. in a humidified atmosphere and concentrated 25–30 fold using an Amicon ultrafiltration assembly with a YM-30 membrane.

Checkerboard analysis was performed to assess the random (chemokinetic) versus the directed (chemotactic) nature of the motility response to autotaxin. Chambers were assembled with different concentrations of ATX above and below the filter, using ATX purified through the weak anion exchange fractionation step. Squares below the diagonal reflect response to a positive gradient, squares above reflect response to a negative gradient, and squares on the diagonal reflect random motility in the absence of a gradient. ATX stimulates both chemotactic and chemokinetic responses (FIG. 10), with chemotactic responses as high as fifteen-fold above background and chemokinesis as high as eight-fold above background.

Amino acid analysis after complete acid hydrolysis was used to quantitate purified protein. This hydrolysis was carried out on protein excised from a polyacrylamide gel and presumed to be pure. The analysis indicated that 2.7 nmol of protein was present after fractionation on the molecular sieve. After fractionation by strong anion exchange chromatography, approximately 300 pmol remained. The results of the analysis are shown in Table 3.

TABLE 3

| AMINO ACID COMPOSITION OF AUTOTAXIN (CYS and TRP were not determined in this analysis) | |
|---|---|
| Amino Acid | Residues/100 |
| ASX | 12.5 |
| THR | 6.0 |
| SER | 5.7 |
| GLX | 9.4 |
| PRO | 7.4 |
| GLY | 7.0 |
| ALA | 3.9 |
| VAL | 6.7 |
| MET | 1.2 |
| ILE | 4.3 |
| LEU | 9.0 |
| TYR | 5.2 |
| PHE | 5.2 |
| HIS | 3.8 |
| LYS | 7.4 |
| ARG | 5.4 |

EXAMPLE 3

ATX Degradation and Determination of Amino Acid Sequence

Figures 10, 11:
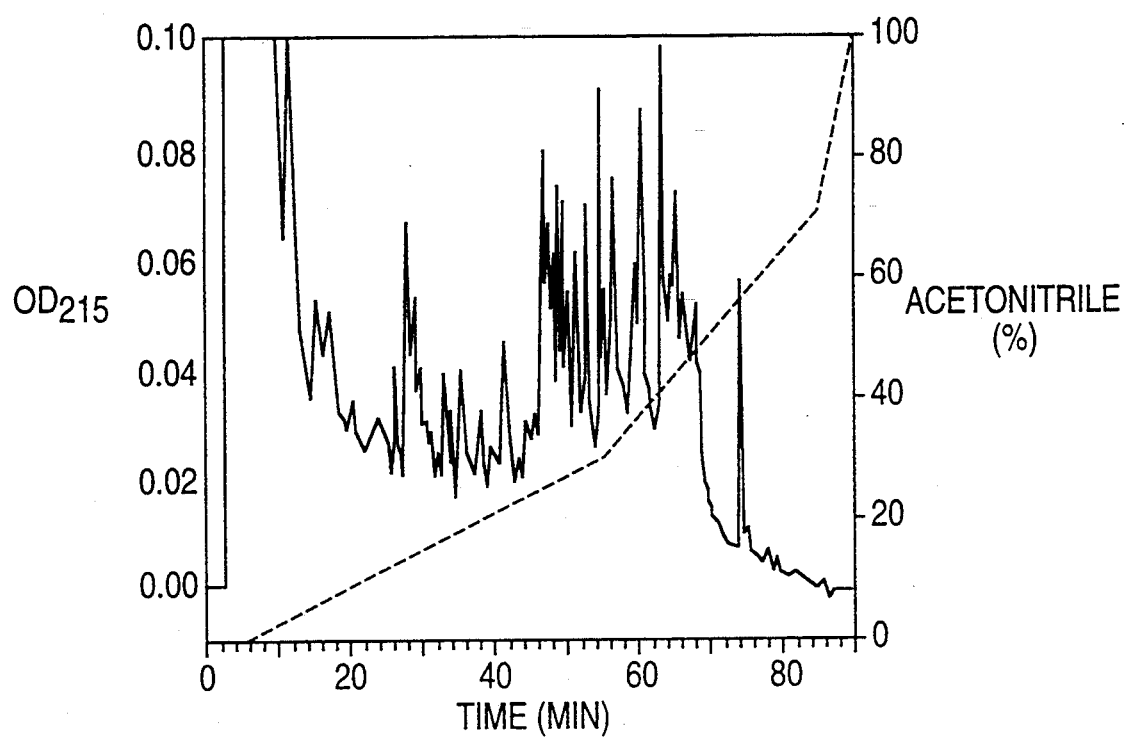
FIG. 10. Checkerboard analysis of ATX-stimulated motility. Varying dilutions of autotaxin were added to the upper chamber with the cells and/or to the lower chamber, as shown. Motility response, expressed as cells/HPF±S.E.M., was assessed for each point in the checkerboard.
FIG. 11. Purification of ATX peptides on HPLC. ATX, purified to homogeneity by strong anionic exchange chromatography, was sequentially digested by cyanogen bromide, subjected to reduction and pyridylethylation, and digested by trypsin. The resulting peptides were purified on an Aquapore RP300 C-8 reverse phase column using a (0–70)% acetonitrile gradient in 0.1% trifluoroacetic acid (----). The absorbance was monitored at 215 nm (_) and peaks were collected. Seven peaks, chosen at random for N-terminal amino acid sequence analysis, are shown with appropriate numbers.

Attempts to obtain N-terminal sequence information from purified ATX repeatedly proved futile. The purified protein was therefore, sequentially digested and the resulting peptides fractionated by reverse phase chromatography. The results are shown in FIG. 11. Multiple sharp peaks including clusters at both the hydrophilic and hydrophobic ends of the gradient are seen.

Several of these peptide peaks were chosen randomly for Edman degradation and N-terminal amino acid sequence analysis. Seven of the eight peaks (shown in FIG. 11) chosen gave clear single sequence information as seen in Table 4. Using material from a separate digestion and purification, the remaining four sequences were also obtained.

Separate sense and antisense oligonucleotide probes were synthesized according to the fragment sequences of Table 4 by methods known to one skilled in the art. Representative probes are shown in Table 5.

TABLE 4

| Peptide sequences for Autotaxin. | | | |
|---|---|---|---|
| PEPTIDE NO. | AMINO ACID SEQUENCE | SEQ ID: NO: | NAME |
| 1. | WHVAAN | SEQ ID NO: 1 | ATX 18 |
| 2. | PXLDVYK | SEQ ID NO: 2 | ATX 19 |
| 3. | YPAFK | SEQ ID NO: 3 | ATX 20 |
| 4. | QAEVS | SEQ ID NO: 4 | ATX 24 |
| 5. | PEEVTXPNYL | SEQ ID NO: 5 | ATX 29 |

TABLE 4-continued

Peptide sequences for Autotaxin.

| PEPTIDE NO. | AMINO ACID SEQUENCE | SEQ ID NO: | NAME |
|---|---|---|---|
| 6. | YDVPWNETI | SEQ ID NO: 6 | ATX 47 |
| 7. | SPPFENINLY | SEQ ID NO: 7 | ATX 48 |
| 8. | GGQPLWITATK | SEQ ID NO: 8 | ATX 100 |
| 9. | VNSMQTVFVGYGPTFK | SEQ ID NO: 9 | ATX 101 |
| 10. | DIEHLTSLDFFR | SEQ ID NO: 10 | ATX 102 |
| 11. | TEFLSNYLTNVDDITLVPGTLGR | SEQ ID NO: 11 | ATX 103 |
| 12. | QYLHQYGSS | SEQ ID NO: 26 | ATX 37 |
| 13. | VLNYF | SEQ ID NO: 27 | ATX 39 |
| 14. | YLNAT | SEQ ID NO: 28 | ATX 40 |
| 15. | HLLYGRPAVLY | SEQ ID NO: 29 | ATX 41 |
| 16. | SYPEILTPADN | SEQ ID NO: 30 | ATX 44 |
| 17. | XYGFLFPPYLSSSP | SEQ ID NO: 31 | ATX 53 |
| 18. | TFPNLYVF/LAQGLYWS | SEQ ID NO: 32 | ATX 59 |
| 19. | VNVISGPIFDYDYDGLH/ADTEDK | SEQ ID NO: 33 | ATX 104 |

Peptide numbers 1-7 refer to peaks numbered in FIG. 11. Peptide numbers 12-18 refer to peptides purified from the preparation which yielded peptide numbers 1-7. Peptides 8-11 and 19, are from a separate purification, not shown in FIG. 11. X refers to potentially glycosylated residues.

TABLE 5

Oligonucleotides synthesized from peptide sequences of autotaxin (ATX). The number of the oligonucleotide corresponds to the ATX peptide number as per Table 4. The final letter suffix distinguishes whether the oligonucleotide is a sense (S) or antisense (A) sequence.

| Oligo | Sequence | SEQ ID NO: |
|---|---|---|
| A-18A | GTT—GGC—AGC—NAC—RTG—CCA | SEQ ID NO: 12 |
| A-18S | TGG—CAY—GTN—GCT—GCC—AAC | SEQ ID NO: 13 |
| A-20A | CTT—GAA—GGC—AGG—GTA | SEQ ID NO: 14 |
| A-20S | TAY—CCT—GCN—TTY—AAG | SEQ ID NO: 15 |
| A-29A | GGT—NAC—YTC—YTC—AGG | SEQ ID NO: 16 |
| A-29S | CCT—GAR—GAR—GTN—ACC | SEQ ID NO: 17 |
| A-47A | NGT—NGC—RTC—RAA—TGG—CAC—RTC | SEQ ID NO: 18 |
| A-47S | GAY—GTG—CCA—TTY—GAY—GCN—ACN | SEQ ID NO: 19 |
| A-48A | GTT—DAT—RTT—STC—RAA—TGG—GGG | SEQ ID NO: 20 |
| A-48S | CCC—CCA—TTT—GAG—AAC—ATC—AAC | SEQ ID NO: 21 |
| A-100A | CTT—NGT—NGC—NGT—DAT—CCA—NAR— | SEQ ID NO: 22 |

TABLE 5-continued

Oligonucleotides synthesized from peptide sequences of autotaxin (ATX). The number of the oligonucleotide corresponds to the ATX peptide number as per Table 4. The final letter suffix distinguishes whether the oligonucleotide is a sense (S) or antisense (A) sequence.

| Oligo | Sequence | SEQ ID NO: |
|---|---|---|
| A-100S | GGG—YTG—GCC—GCC GGC—GGC—CAR—CCC—YTN—TGG—ATH—ACN—GCN—ACN—AAG | SEQ ID NO: 23 |
| A-101A | CTT—RAA—GGT—GGG—GCC—RTA—GCC—CAC—RAA—GAC—TGT—YTG—CAT | SEQ ID NO: 24 |
| A-101S | ATG—CAR—ACA—GTC—TTY—GTG—GGC—TAY—GGC—CCC—ACC—TTY—AAR | SEQ ID NO: 25 |

EXAMPLE 4

Molecular Cloning of Autotaxin cDNA

A cDNA library was prepared in phage ($\lambda_{zap}$) from the same A2058 tumor cells known to synthesize ATX. This library has been screened for the presence of the ATX sequence by the following methods. First, a 200 base pair (bp) sequence of DNA was prepared using PCR (polymerase chain reaction) technology with the same $\lambda_{zap}$ library as template and the derived oligonucleotides A-48S (SEQ ID NO:21) and A-100A (SEQ ID NO:22) as priming sequences. This 200 bp sequence of the ATX mRNA has been used to perform initial screens of the full library. Alternatively, a mixture of derived oligonucleotides was also used to screen the full cDNA library. Both screening methods have produced positive cDNA clones.

EXAMPLE 5

Antipeptide Antibodies

Rabbits were injected with ATX-101 (SEQ ID NO:10) which had been cross-linked to bovine serum albumin. Antisera from these rabbits was subjected to salt precipitation followed by purification using affinity chromatography with Affi-Gel 10 beads covalently linked to the peptide, ATX-101 (SEQ ID NO:10). This affinity purified antibody reacted with the partially purified protein on immunoblots. This same antibody has been used to perform immunohistochemical stains on human tissue.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the present invention and appended claims.

What is claimed is:

1. A polypeptide selected from human autotaxin protein in homogeneous form, wherein
   (A) said protein has an isoelectric point of about 7.7, a molecular weight of about 125 kDa, as determined SDS-polyacrylamide gel electrophoresis under reducing conditions, and induces a motility in human A2058 melanoma cells which is inhibited by pertussis toxin; and
   (B) antibody suitable for immunohistochemical staining of cancerous human tissue can be raised to said protein.

2. The polypeptide of claim 1, wherein said human autotaxin protein has the amino acid sequence of an autotaxin protein isolated from human A2058 melanoma cells.

3. A polypeptide comprising an amino acid sequence selected from the group consisting of SEQ ID NOs. 1, 3, 4, 6–11, 26–30 and 32–33 wherein an antibody suitable for immunohistochemical staining of cancerous human tissue can be raised to said polypeptide.

* * * * *